United States Patent [19]

Seguin et al.

[11] Patent Number: 5,607,471
[45] Date of Patent: Mar. 4, 1997

[54] PROSTHETIC RING FOR HEART SURGERY

[75] Inventors: Jacques Seguin, Hôtel de Manse, 4 rue Embouque d'Or, 34000 Montpellier; Robert Rogier, Montpellier, both of France

[73] Assignee: Jacques Seguin, Montpellier, France

[21] Appl. No.: 507,127

[22] Filed: Aug. 21, 1995

Related U.S. Application Data

[63] Continuation of Ser. No. 139,751, Oct. 22, 1993, abandoned.

[30] Foreign Application Priority Data

Aug. 8, 1993 [FR] France .................................... 93 09768

[51] Int. Cl.⁶ ........................................................ A61F 2/24
[52] U.S. Cl. ..................................... 623/2; 623/900
[58] Field of Search .............................. 623/2, 18, 900

[56] References Cited

U.S. PATENT DOCUMENTS

| | | |
|---|---|---|
| 3,656,185 | 4/1972 | Carpentier . |
| 4,035,849 | 7/1977 | Angell et al. ........................ 623/2 |
| 4,042,979 | 8/1977 | Angell . |
| 4,055,861 | 11/1977 | Carpentier et al. ................... 623/2 |
| 4,204,283 | 5/1980 | Bellhouse .............................. 623/2 |
| 4,217,665 | 8/1980 | Bex et al. ............................. 623/2 |
| 4,290,151 | 9/1981 | Massana . |
| 4,489,446 | 12/1984 | Reed . |
| 4,561,129 | 12/1985 | Arpeslla .............................. 623/2 |
| 4,602,911 | 7/1986 | Ahmadi et al. ...................... 623/2 |
| 4,655,773 | 4/1987 | Grassi ................................. 623/2 |
| 4,743,261 | 5/1988 | Epinette ............................. 623/18 |
| 4,917,698 | 4/1990 | Carpentier et al. . |
| 5,061,277 | 10/1991 | Carpentier et al. ................... 623/2 |
| 5,104,407 | 4/1992 | Lam et al. . |
| 5,290,300 | 3/1994 | Cosgrove et al. ................. 623/2 X |

FOREIGN PATENT DOCUMENTS

| | | |
|---|---|---|
| 338994 | 10/1989 | European Pat. Off. . |
| 1264472 | 2/1972 | United Kingdom . |

OTHER PUBLICATIONS

Duran, "The Annals of Thoracic Surgery," vol. 22, No. 5, pp. 458–463 (1976).

Primary Examiner—Robert A. H. Clarke
Attorney, Agent, or Firm—Oliff & Berridge

[57] ABSTRACT

A prosthetic ring includes a core enclosed in a textile sheath, the sheath being sutured to the heart or the aorta of a patient. The core includes at least one relatively rigid portion and one portion that is relatively flexible compared to the rigid portion. The cross-sectional diameter of the core varies along the circumference of the ring, decreasing from a maximum at the rigid portion to a minimum at the flexible portion, giving the ring sufficient flexibility to accommodate heart wall movement.

16 Claims, 3 Drawing Sheets

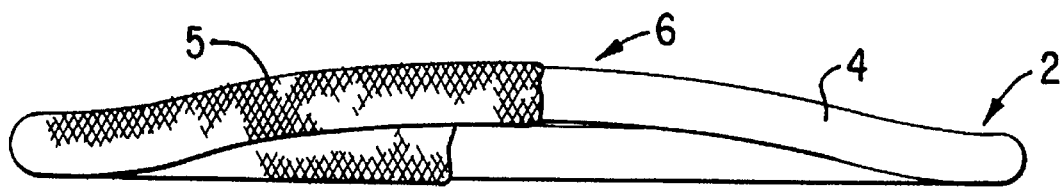
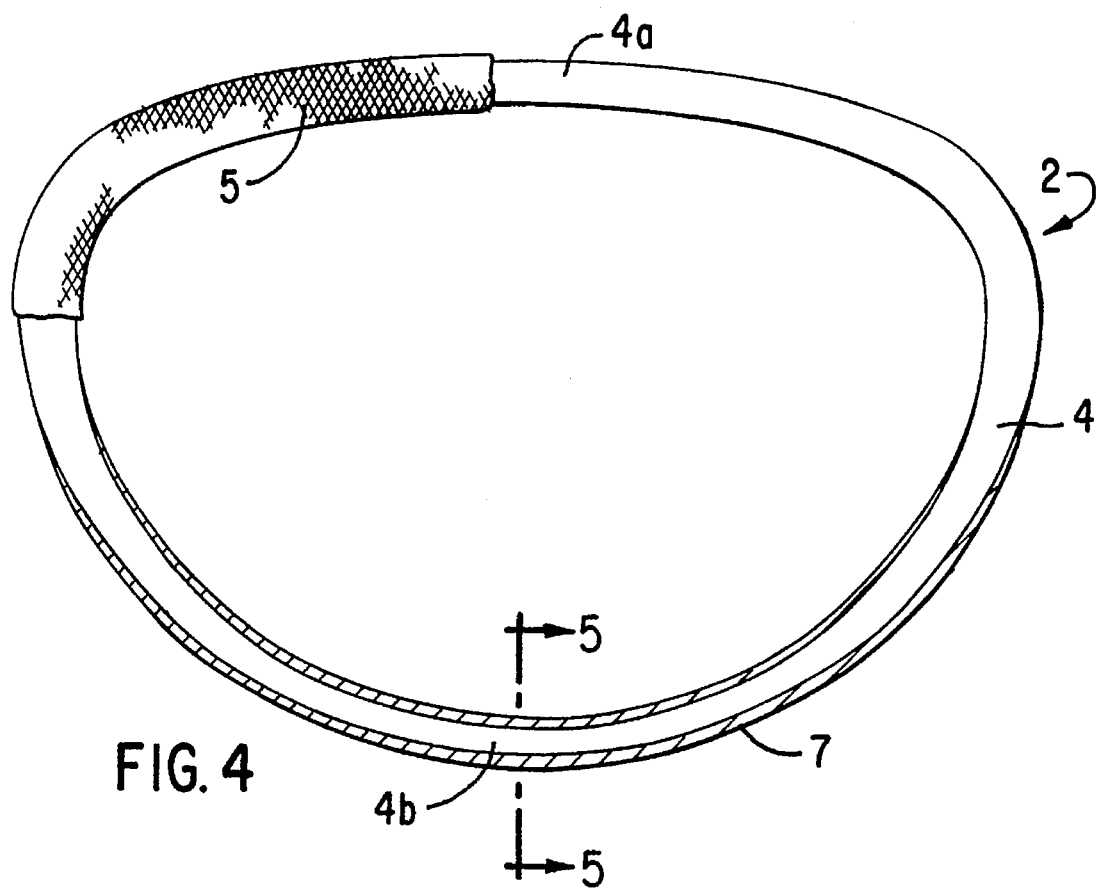
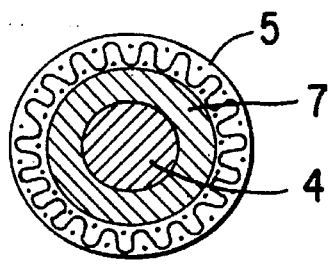

PROSTHETIC RING FOR HEART SURGERY

This a continuation of application Ser. No. 08/139,751 filed Oct. 22, 1993, now abandoned.

BACKGROUND OF THE INVENTION

The present invention relates to a prosthetic ring for heart surgery, particularly for mitral, tricuspid, or aortic annuloplasty.

In normal mitral, tricuspid, or aortic valves, the valves overlap at the center of the fibromuscular ring that surrounds the valve, ensuring that the valve prevents backflow of blood from the ventricle to the atrium or from the aorta to the ventricle. Various diseases can cause deformation or dilation of these rings, causing a leak in the valves and, hence, backflow of blood. As long as ring deformation is not too great, it is preferable to surgically reconstruct the ring rather than replace the total valve.

A prosthetic ring designed for this purpose includes a core covered with a sheath of blood-compatible textile material. The core must have sufficient rigidity to reduce deformation or dilation of the biological ring without disturbing, to the extent possible, the natural opening and closing movements of the valve. The sheath allows the prosthesis to be sutured to the wall of the heart or aorta.

Several prosthetic ring models have been developed in the last two decades.

The earliest implants, described, for example, in U.S. Pat. No. 3,656,185 to Carpentier, are annular or partially annular rigid implants. The rigidity of these rings allows dilation of the biological ring to be reduced and restores a satisfactory shape to it, but, on the other hand, has the drawback of resisting the natural flexibility of the ring of the posterior mitral valve and the tricuspid septal valve, which can lead to dysfunction of these valves. In addition, these rigid-ring prostheses offer resistance to the natural movements of the wall of the heart, so that sutures in the heart wall are stressed and hence subjected to wear and stretching.

On the other hand, certain designers have proposed extremely flexible prosthetic rings, such as those described in U.S. Pat. No. 4,290,151 to Massana, and in the papers by Duran published in the journal "The Annals of Thoracic Surgery," Vol. 22, No. 5, 458–463 (1976). U.S. Pat. No. 4,042,979 to Angell also proposes a flexible ring, which can be adjusted during surgery to a desired geometry. These highly flexible rings allow too much fibromuscular ring deformation and do not always restore satisfactory coaptation of these valves.

U.S. Pat. No. 4,489,446 to Reed describes a ring composed of two nested rigid elements, which slide into each other upon each contraction of the heart, allowing the ring to deform in its plane. This ring has the drawbacks of 1) being too rigid and 2) resisting heart movements perpendicular to the plane of the ring.

More recently, prosthetic rings with portions of different rigidities at their circumference have been proposed.

U.S. Pat. No. 4,917,698 to Carpentier describes a prosthetic ring, composed by assembling two segments for a mitral valve and three segments for a tricuspid valve. The segments are connected to each other and articulated with each other by means of a flexible textile link that passes through them. One of the segments of this ring is rigid and made of titanium alloy, while the other segment or segments is/are flexible and made of a synthetic material known as DELRIN. Several flexible segments with different dimensions can be connected to one rigid segment to constitute a ring, to allow the flexibility of the flexible portion of the ring to be modulated, as needed.

U.S. Pat. No. 5,061,277 to Carpentier and Lane describes another ring having a rigid part made of a titanium alloy and a flexible silicone part. These parts are also connected together by a flexible link made of a textile material. In both cases, this link has the drawback of possibly being subject to wear and thus affecting, over time, the strength of the implant.

U.S. Pat. No. 5,104,407 to Lam, Nguyen, and Carpentier describes a ring having an inner part made of a spiral winding of fine fibers of a cobalt-nickel alloy known under the trademark ELGILOY. The various layers of fibers overlap in a rigid part and are separated from each other by an elastomeric material in a more flexible part. The number of fiber layers varies according to the elasticity to be obtained. This structure allows better distribution, over the periphery of the ring, of the stresses exerted by the heart muscle. Because of its structure, however, this ring appears to be difficult to deform, other than in its plane, while the biological ring is also subjected to deformation perpendicular to its plane. The rigidity in this direction also interferes with certain components of the natural heart movement. Moreover, this ring appears to be complex and difficult to manufacture.

SUMMARY OF THE INVENTION

The present invention remedies these drawbacks. A prosthetic ring according to the invention adjusts to the shape of the biological ring very well, without interfering with natural heart movement, and is simple to manufacture.

BRIEF DESCRIPTION OF THE DRAWINGS

Preferred embodiments are described with reference to the drawings, in which like reference numerals denote like elements throughout the Figures, and in which:

FIG. 3 is a side view of a ring intended for mitral annuloplasty, according to another embodiment of the invention;

FIG. 4 is a plan view of a ring intended for mitral annuloplasty, partially sectioned in its plane, according to another embodiment of the invention;

FIG. 5 is a cross-sectional view along line 5—5 of FIG. 4;

DETAILED DESCRIPTION OF PREFERRED EMBODIMENTS

Figure 1:
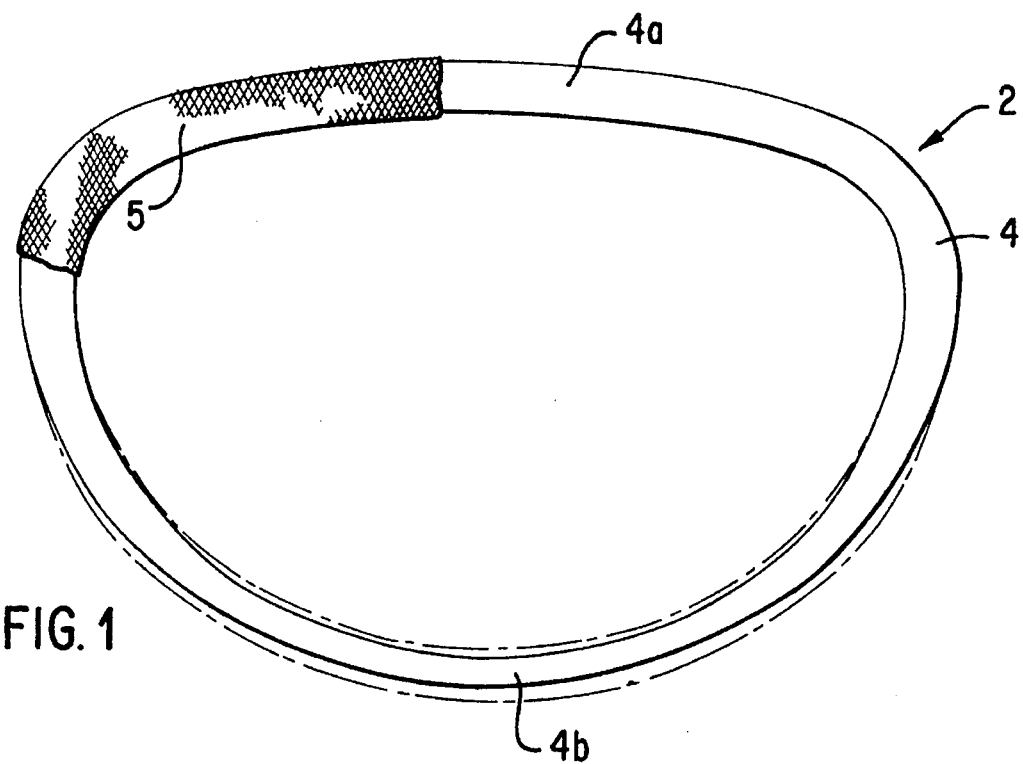
FIG. 1 is a plan view of a ring intended for mitral annuloplasty, according to an embodiment of the invention.

Rings according to the invention include a core, engaged in a textile sheath constituting a suturing means. The core forms a ring, which can be complete or incomplete, and includes at least one relatively rigid portion and one portion that is flexible relative to the rigid portion.

According to the invention, a cross-sectional diameter of the core varies along the circumference of the ring, decreasing from a maximum at the rigid portion to a minimum at the flexible portion, and permitting deformation of the ring in all planes. This decrease achieves core flexibility far more simply than in prior art prostheses.

The cross-sectional diameter may decrease along at least one transverse direction, specifically along a thickness and/ or a height of the core, symmetrically or asymmetrically relative to its center.

The prosthesis according to the invention has sufficient rigidity to reduce dilation of the biological ring and to restore a satisfactory geometry thereto. The prosthesis also has, at an appropriate location, flexibility that allows it to not counteract natural heart movement. Hence, the heart places little stress on sutures that attach the prosthesis to the wall of the heart or the aorta.

The core can be formed by assembling two segments of appropriate material, for example, a segment made of titanium alloy to constitute the rigid portion, and a segment made of synthetic material to constitute the flexible portion. However, it is advantageously of integral design, that is, made of a single piece. In addition to increased ease of manufacture, such a core presents little or no risk of wear or breakage at links of the segments, despite the repeated stresses it undergoes, unlike prior art cores formed by assembling several segments of different materials.

Preferably, the decrease in cross-sectional diameter is gradual and either regular or irregular, that is, either smooth or stepped, to achieve a gradual change in the flexibility of the core and to uniformly distribute, around the circumference of the core, the stresses exerted by the wall of the heart or aorta.

According to a first possibility, the core is constituted by molding a synthetic material, preferably a linear polyoxymethylene-type acetal resin known under the trademark DELRIN. According to another possibility, the core is made of the titanium alloy known as TA6V, which is generally used for prostheses.

The flexible part of the core may be supplemented by an insert made of an elastomeric material, to reinforce the core and to offset the decrease in its cross-sectional diameter, if necessary.

The ring can also include a radiopaque element so that it can be made visible during radiography.

Prosthetic rings 2, 3, and 10 each have a general anatomical shape. Ring 2, intended for reconstruction of the biological mitral ring, has essentially a "D" shape. Ring 3, intended for reconstruction of the biological tricuspid ring, is substantially ovoid. Ring 10, intended for reconstruction of the biological aortic ring, includes three curved portions connected to each other by commissures substantially perpendicular to the plane of the ring.

Each ring 2, 3 includes core 4 enclosed in a blood-compatible textile sheath 5, which provides a means for suturing the ring to the wall of the heart. Core 4 has relatively rigid portion 4a and portion 4b that is relatively flexible, compared to portion 4a. As clearly shown in FIGS. 1–5, for example, core 4 preferably is formed of a single element.

Figure 2:
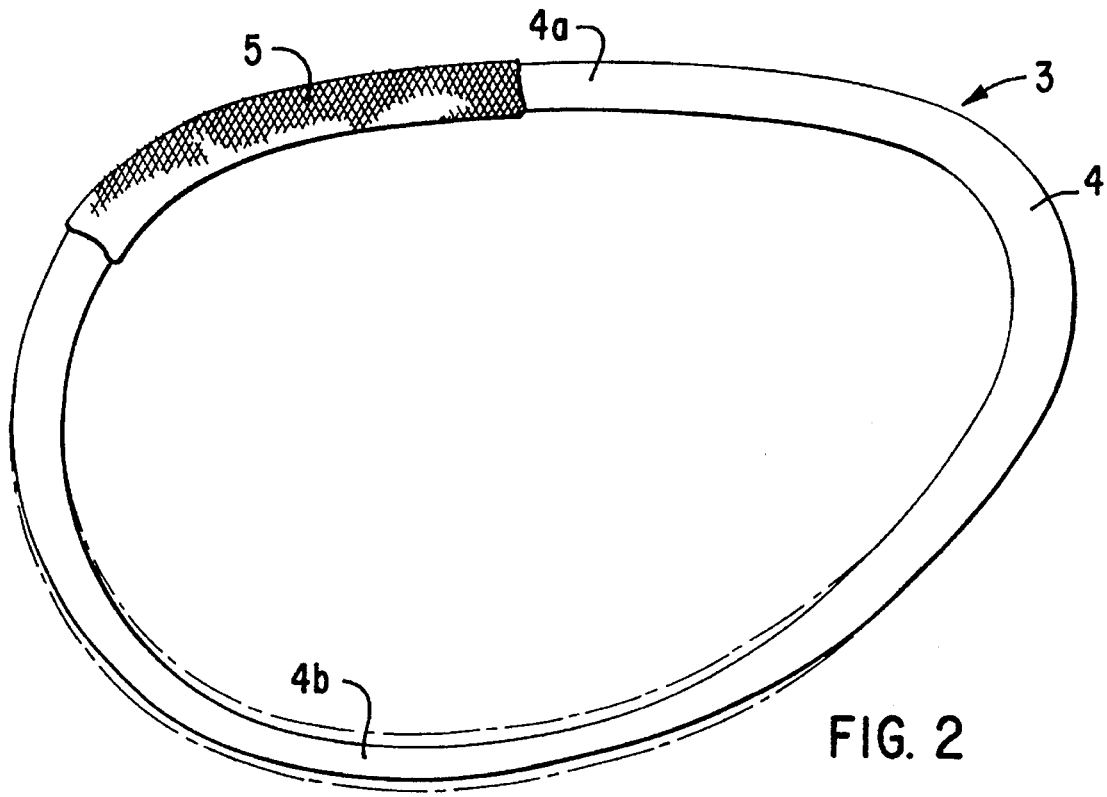
FIG. 2 is a plan view of a ring intended for tricuspid annuloplasty, according to another embodiment of the invention.
Figure 6:
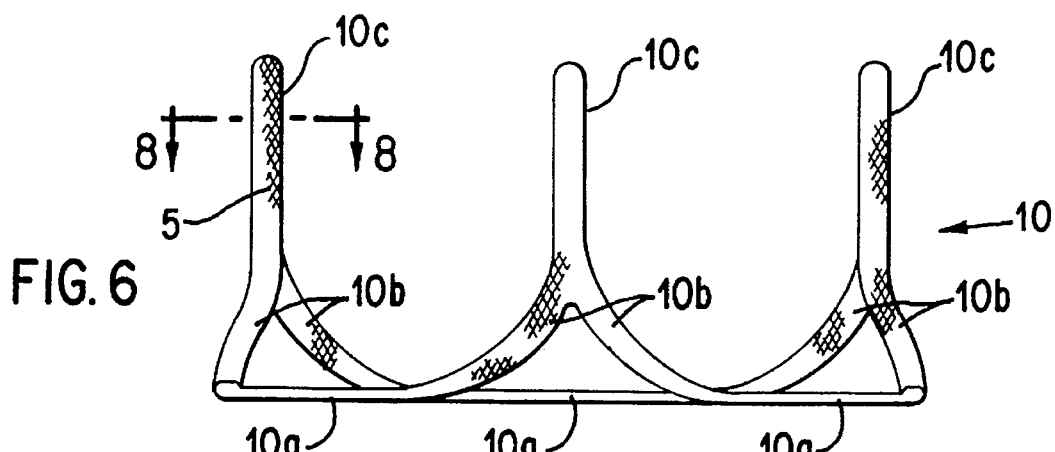
FIG. 6 is a side view of a ring intended for aortic annuloplasty according to another embodiment of the invention.
Figure 7:
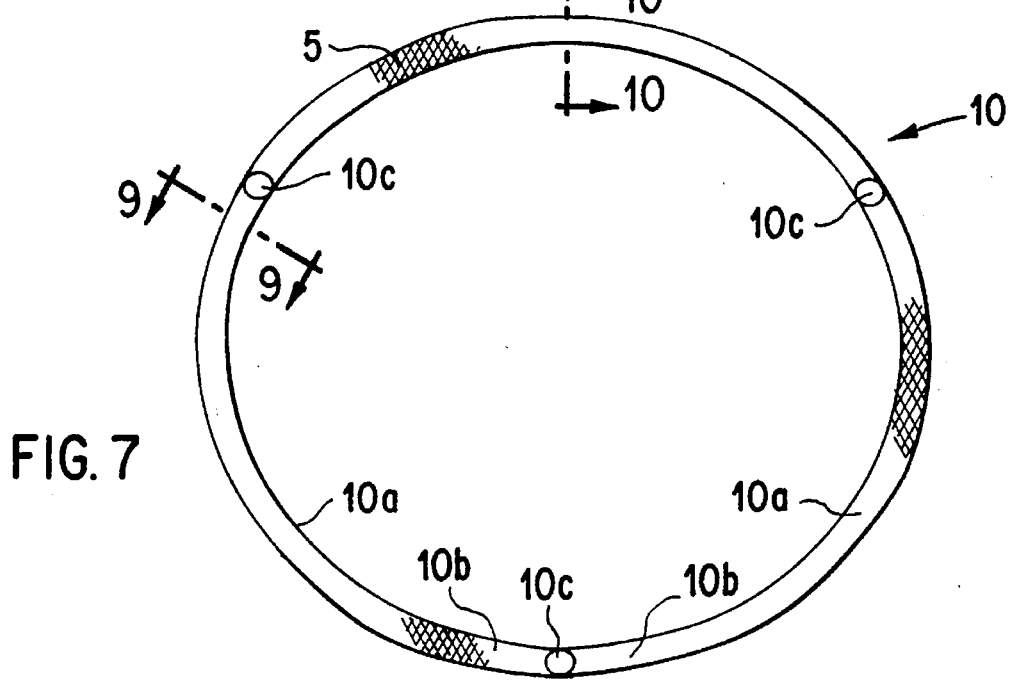
FIG. 7 is a plan view of the ring illustrated in FIG. 6.
Figure 8:
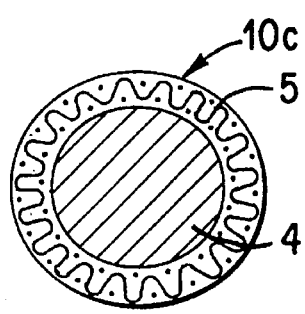
FIG. 8 is a cross-sectional view along line 8—8 of FIG. 6.
Figure 9:
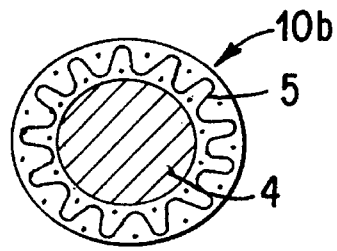
FIGS. 9 is a cross-sectional view along line 9—9 of FIG. 7.
Figure 10:
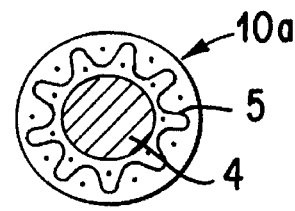
FIG. 10 is a cross-sectional view along line 10—10 of FIG. 7.

As shown in FIGS. 1 and 2 in dot-dashed lines, the cross-sectional diameter of core 4 changes gradually along the circumference of each ring 2, 3. That is, it decreases gradually from a maximum at its stiffest portion 4a, in the direction of its most flexible portion 4b, to a minimum located essentially opposite the median part of the stiffest portion 4a.

As shown in FIG. 5, the cross-section of core 4 is circular. The cross-sectional diameter decreases in terms of both the thickness of core 4, that is, in the plane of each ring 2, 3, and of the height of core 4, that is, perpendicular to the plane of each ring 2, 3.

Each core 4 has an integral structure, that is, it is made of a single piece of material, preferably by molding a synthetic material such as that known under the trademark DELRIN.

This decrease in cross-sectional diameter allows a desired flexibility of core 4 to be obtained at an appropriate location, in a manner that is very easy to manufacture.

Prosthetic ring 2, 3 has sufficient rigidity to reduce dilation of the biological ring and restore it to a satisfactory shape, while having, at the appropriate location, the flexibility that allows it to not resist natural heart movements. The sutures by which the ring is attached to the wall of the heart, therefore, undergo little stress.

Because of the decrease in the cross-sectional diameter of core 4 both in thickness and in height, flexibility of each ring 2, 3 is obtained both in its plane and perpendicular to its plane. This dual deformation renders each ring 2, 3 according to the invention fully functional.

FIG. 3 shows a ring for mitral annuloplasty having the same composition as ring 2 shown in FIG. 1, except that it has a deformation 6 outside its plane, located at the rigid part 4a of core 4. This deformation 6 is symmetrical relative to the anteroposterior axis of the ring. Ring 2, with deformation 6, has the advantage of adjusting better to the natural geometry of the biological ring.

FIG. 4 shows another embodiment of mitral ring 2. Here, too, the elements described above are designated by the same reference numerals in this embodiment. In this mitral ring 2, core 4 is made of a titanium alloy known as TA6V. To obtain the appropriate flexibility, the decrease in the cross-sectional diameter of core 4 at part 4b is large, as shown in FIG. 5. This decrease is then offset by an insert 7 made of biocompatible elastomeric material, which reinforces core 4 at this point. The inside cross-section of insert 7 changes to match that of core 4, giving ring 2 an essentially constant outer cross-section.

FIGS. 6 to 10 show ring 10, intended for aortic annuloplasty.

Ring 10 has three curved portions 10a connected to each other by commissures 10b, oriented essentially perpendicularly to the plane of ring 10. Commissures 10b are extended by contact fingers 10c that allow attachment to the corresponding area of the aortic ring and the wall of the aorta, thereby constituting a new surgical technique. In the same manner as described above, ring 10 includes core 4 engaged in a textile sheath 5 for suturing. Core 4 is formed by molding a thermoplastic synthetic material such as that known under the trademark DELRIN.

As shown in FIGS. 7 to 10, the cross-sectional diameter of core 4 changes along ring 10 within each curved portion 10a. It is minimal at the median part of each of these curved portions 10a and increases in the direction of commissures 10b.

In the same manner as for rings 2, 3, described above, ring 10 allows dilation of the biological aortic ring to be reduced. Ring 10 confers a shape to the biological ring that allows the valves to be covered, while having sufficient flexibility to not counteract heart movement. Ring 10, therefore, is fully functional.

While the invention has been described with reference to specific embodiments, the description is illustrative and is not to be construed as limiting the scope of the invention. Various modifications and changes may occur to those skilled in the art without departing from the spirit and scope of the invention as defined in the following claims.

What is claimed is:

1. A prosthetic ring for at least one of mitral, tricuspid and aortic annuloplasty, comprising a core enclosed in a textile sheath, wherein:

the sheath comprises a suturing means;

the core is formed from a single material, the core comprises at least one relatively rigid portion and at least one flexible portion that is flexible relative to the rigid portion; and a cross-sectional area of the core varies along a circumference of the ring, the area decreasing from the rigid portion toward the flexible portion, allowing deformation of the ring in all planes passing through the ring.

2. The prosthetic ring of claim 1, wherein at least one of a thickness and a height of the core decreases as the core area decreases.

3. The prosthetic ring of claim 1, wherein the cross-sectional area of the core decreases asymmetrically with respect to a center of the core.

4. The prosthetic ring of claim 1, wherein the cross-sectional area of the core decreases symmetrically with respect to a center of the core.

5. The prosthetic ring of claim 1, wherein the cross-sectional area of the core is stepped along the circumference of the ring.

6. The prosthetic ring of claim 1, wherein the cross-sectional area of the core is smooth along the circumference of the ring.

7. The prosthetic ring of claim 1, wherein the core is formed by molding a synthetic material.

8. The prosthetic ring of claim 7, wherein the synthetic material is a linear polyoxymethylene acetal resin.

9. The prosthetic ring of claim 1, wherein the core is formed of a titanium alloy.

10. The prosthetic ring of claim 1, wherein the core is assembled of at least two segments of material, one of the segments including the rigid portion of the core and another of the segments including the flexible portion of the core.

11. The prosthetic ring of claim 1, wherein the flexible portion of the core is reinforced by an insert of elastomeric material.

12. The prosthetic ring of claim 1, comprising a radiopaque element.

13. A ring intended for mitral annuloplasty, comprising:

a sheath; and a core enclosed in the sheath;

wherein the core has a shape generally in the form of a "D", the core is formed from a single piece of synthetic material and comprises a relatively rigid portion and a flexible portion, wherein the flexible portion is flexible relative to the rigid portion;

the flexible portion is essentially opposite the rigid portion; and a cross-sectional area of the core varies from a maximum area at the stiffest portion of the core to a minimum area located essentially opposite a median part of the stiffest portion of the core.

14. A ring intended for tricuspid annuloplasty, comprising:

a sheath; and a core enclosed in the sheath;

wherein the core has an essentially ovoid shape, the core is formed from a single piece of synthetic material and comprises a relatively rigid portion and a flexible portion, wherein the flexible portion is flexible relative to the rigid portion;

the flexible portion is situated essentially opposite the rigid portion; and a cross-sectional area of the core varies from a maximum area at the stiffest portion of the core to a minimum area located essentially opposite a median part of the stiffest portion of the core.

15. A ring intended for aortic annuloplasty, comprising a sheath; and a core enclosed in the sheath;

wherein the core is formed from a single piece of synthetic material and the core includes three curved portions connected to each other by commissures substantially perpendicular to a plane of the ring;

each curved portion comprising a relatively rigid portion and a flexible portion, wherein the flexible portion is flexible relative to the rigid portion; and a cross-sectional area of the core changes along the ring, the cross-sectional area is minimal at a median part of each of the curved portions, the median part of each curved portion forms the flexible portion, and the cross-sectional area increases in the direction of the commissures forming the rigid portion.

16. A prosthetic ring for at least one of mitral, tricuspid and aortic annuloplasty, comprising a core enclosed in a textile sheath, wherein:

the sheath comprises a suturing means;

the core is integrally formed of one piece, the core comprises at least one relatively rigid portion and at least one flexible portion that is flexible relative to the rigid portion; and a cross-sectional area of the core varies along a circumference of the ring, the area decreasing from the rigid portion toward the flexible portion, allowing deformation of the ring in all planes passing through the ring.

* * * * *